(12) United States Patent
Park et al.

(10) Patent No.: US 7,662,613 B2
(45) Date of Patent: Feb. 16, 2010

(54) DISEASE DIAGNOSIS APPARATUS AND METHOD USING PHOTOCURRENT OF AMORPHOUS SILICON

(75) Inventors: Se-Ho Park, Daejon (KR); Moon-Youn Jung, Daejon (KR); Hyeon-Bong Pyo, Daejon (KR)

(73) Assignee: Electronics and Telecommunications Research Institute, Daejon (KR)

( * ) Notice: Subject to any disclaimer, the term of this patent is extended or adjusted under 35 U.S.C. 154(b) by 0 days.

(21) Appl. No.: 12/099,321

(22) Filed: Apr. 8, 2008

(65) Prior Publication Data

US 2009/0017458 A1 Jan. 15, 2009

(30) Foreign Application Priority Data

Jul. 10, 2007 (KR) .................... 10-2007-0069045

(51) Int. Cl.
*C12M 3/00* (2006.01)
(52) U.S. Cl. ................................... 435/287.2
(58) Field of Classification Search ................ None
See application file for complete search history.

(56) References Cited

U.S. PATENT DOCUMENTS 4,077,845 A * 3/1978 Johnson ................. 435/33
5,563,356 A * 10/1996 Mussi et al. ............. 73/864.14
2002/0081716 A1* 6/2002 Yagi ........................ 435/287.2
2004/0078852 A1* 4/2004 Thomashow et al. ........ 800/289
2006/0105357 A1* 5/2006 Benesch et al. ................ 435/6

FOREIGN PATENT DOCUMENTS

| KR | 10-0375105 | 2/2003 |
|----|------------|--------|
| KR | 2004-0035104 A | 4/2004 |
| KR | 10-0613138 | 8/2006 |
| WO | WO 03/102554 A1 | 12/2003 |

OTHER PUBLICATIONS

Fixe et al. ["An on-chip thin film photodetector for the quantification of DNA probes and targets in microarrays", Nucleic Acids Research, 2004, vol. 32, No. 9].*
Fortunato et al., "Amorphous silicon sensors: from photo to chemical detection", Journal of Non-Crystalline Solids, vol. 227-230, pp. 1349-1353, 1998.
Fixe et al., "An on-chip thin film photodetector for the quantification of DNA probes and targets in microarrays", Oxford University Press, Nucleic Acids Research, vol. 32, No. 9, pp. 1-6, May 2004.

* cited by examiner

*Primary Examiner*—Ann Y Lam
(74) *Attorney, Agent, or Firm*—Rabin & Berdo, P.C.

(57) ABSTRACT

Provided is a disease diagnosis apparatus and method for detecting a specific disease. The disease diagnosis chip, includes: a light sensing layer; a probe molecule fixed on the light sensing layer; and an electrode connected to the light sensing layer to detect an electric signal corresponding to photoelectric charges of the light sensing layer.

13 Claims, 5 Drawing Sheets

DISEASE DIAGNOSIS APPARATUS AND METHOD USING PHOTOCURRENT OF AMORPHOUS SILICON

CROSS-REFERENCE(S) TO RELATED APPLICATIONS

The present invention claims priority of Korean Patent Application No. 10-2007-0069045, filed on Jul. 10, 2007, which is incorporated herein by reference.

BACKGROUND OF THE INVENTION

1. Field of the Invention

The present invention relates to a disease diagnosis apparatus and method for detecting a specific disease; and, more particularly, to a disease diagnosis apparatus and method for quantitatively diagnosing a disease by using amorphous silicon that generates a photocurrent.

This work was supported by the IT R&D program for MIC/IITA [2006-S-007-01, "Ubiquitous Health Monitoring Module and System Development"].

2. Description of Related Art

A disease diagnosis apparatus using paper chromatography, such as a pregnancy diagnosis kit or a marker protein diagnosis kit commercially available in the markets, is considered as being worthy in terms of convenience and economical efficiency.

However, the disease diagnosis apparatus using the paper chromatography has disadvantages in that it cannot measure the concentration of a target molecule, which is a specific biomaterial to be detected, and it degrades a reproduction, which is an ability to accurately express a relationship between a chromogenic signal and a target molecule concentration. This is because when a sample moves in a paper used in the paper chromatography, non-uniformity occurs in the movement of the target molecule such as protein.

Furthermore, the disease diagnosis apparatus using the paper chromatography has a disadvantage in that users should directly determine from a chromogenic signal whether a test result is positive or negative. That is, when the chromogenic signal is unclear, the determination results of the users may be different.

SUMMARY OF THE INVENTION

An embodiment of the present invention is directed to providing a disease diagnosis apparatus and method that can detect a target molecule and measure a concentration of the target molecule.

Another embodiment of the present invention is directed to providing a disease diagnosis apparatus and method that can output a test result expressed as a quantitative value.

Another embodiment of the present invention is directed to providing a disease diagnosis apparatus and method that can improve a reproduction in detecting a target molecule and measuring a concentration of the target molecule.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

In accordance with an aspect of the present invention, there is provided a disease diagnosis chip, including: a light sensing layer; a probe molecule fixed on the light sensing layer; and an electrode connected to the light sensing layer to detect an electric signal corresponding to photoelectric charges of the light sensing layer.

The disease diagnosis chip of the present invention, further includes: a light transmitting layer disposed on the light sensing layer to cover the electrode and the light sensing layer and a light blocking layer disposed on the light sensing layer in a region other than a region where the probe molecule is fixed.

The disease diagnosis chip of the present invention, further includes: a fluid tube covering the probe molecule and guiding an introduced sample to the probe molecule and the probe molecule is formed of a material selected from the group consisting of antigen, antibody, DNA, RNA, lectin, protein, peptides, and saccharide.

The disease diagnosis chip of the present invention, further includes: an amperemeter or voltmeter measuring the electric signal corresponding to an electric signal corresponding to the photoelectric charges generated from the light sensing layer.

In accordance with another aspect of the present invention, there is provided a disease diagnosis method, including the steps of: preparing a light sensing layer; fixing a first probe molecule on the light sensing layer; forming a complex by reacting a solution containing a mixture of an enzyme-attached second probe molecule and a sample of a target molecule with the first probe molecule; forming a precipitate layer on the light sensing layer by reacting a chromogenic reagent with the enzyme attached to the second probe molecule of the complex; and radiating light onto the light sensing layer where the precipitate layer is formed, and measuring an electric signal corresponding photoelectric charges generated from the light sensing layer. Herein, the light sensing layer is formed of a hydrogenated amorphous silicon layer by plasma enhanced chemical vapor deposition (PECVD), and the first and second probe molecule are formed of a material selected from the group consisting of antigen, antibody, DNA, RNA, lectin, protein, peptides, and saccharide.

In the disease diagnosis method of the present invention, an amount of light transmitted to the light sensing layer is controlled by thickness or concentration of the precipitate layer formed on the light sensing layer, and after measuring the photocurrent generated from the light sensing layer, a presence or absence of disease and a concentration of the target molecule can be measured by comparing the measured photocurrent with a target molecule concentration-photocurrent standard curve which is pre-measured.

In accordance with another aspect of the present invention, there is provided a disease diagnosis apparatus, including: a disease diagnosis chip including: a light sensing layer; a probe molecule fixed on the light sensing layer; and an electrode connected to the light sensing layer to detect an electric signal corresponding to photoelectric charges of the light sensing layer; and a body in which the disease diagnosis chip is fixed, the body including: a sample inlet where a sample is introduced; a channel for guiding the introduced sample to the disease diagnosis chip; and a measuring device for measuring a photocurrent generated from the disease diagnosis chip. Herein, two or more disease diagnosis chips are provided for determining if a plurality of diseases exist and measuring the target molecule, and at least one of the two or more disease diagnosis chips is a test chip for testing if an error occurs in an antigen-antibody reaction. The measuring device has a function of converting the measured photocurrent value into a quantitative digital value.

Accordingly, the disease diagnosis apparatus in accordance with the present invention can determine the presence or absence of disease and measure the concentration of the target molecule. Since the disease diagnosis apparatus outputs the measurement result expressed as the quantitative value, an error can be reduced when the users determine the test results. Furthermore, the reproduction of the disease diagnosis apparatus can be improved by moving the sample through the fluid tube.

DESCRIPTION OF SPECIFIC EMBODIMENTS

Figure 1:
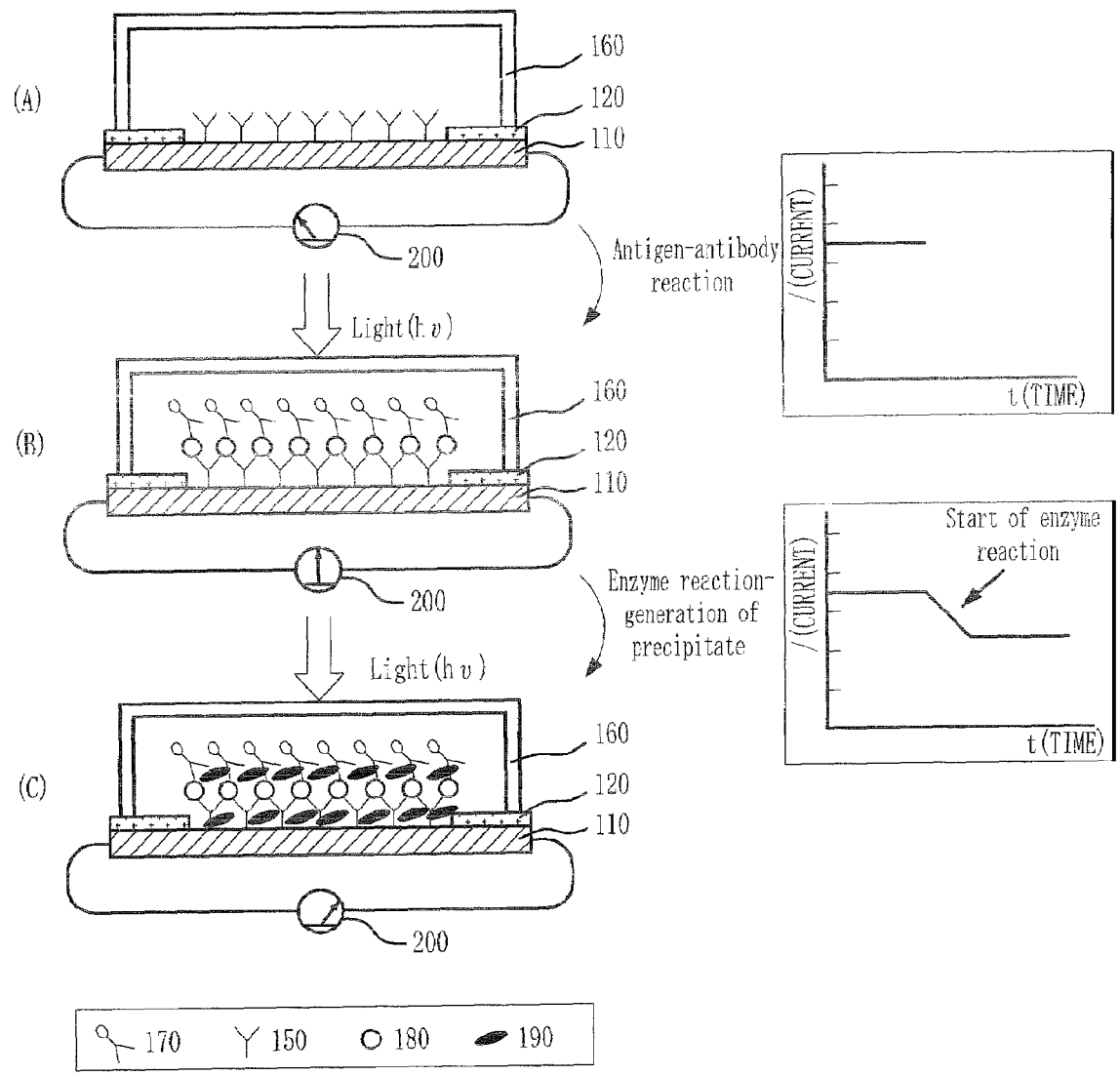
FIG. 1 illustrates a disease diagnosis principle and a disease diagnosis method in accordance with an embodiment of the present invention.

The advantages, features and aspects of the invention will become apparent from the following description of the embodiments with reference to the accompanying drawings, which is set forth hereinafter. Therefore, those skilled in the field of this art of the present invention can embody the technological concept and scope of the invention easily. In addition, if it is considered that detailed description on a related art may obscure the points of the present invention, the detailed description will not be provided herein. The preferred embodiments of the present invention will be described in detail hereinafter with reference to the attached drawings.

In accordance with embodiments of the present invention, target molecule detection and a target molecule concentration measurement can be achieved by radiating natural light or light with specific single wavelength onto a light sensing material, for example, hydrogenated amorphous silicon, and measuring a magnitude of a photocurrent generated from the hydrogenated amorphous silicon. A physical property of hydrogenated amorphous silicon used herein will be described in order to fully understand the present invention.

Hydrogenated amorphous silicon used as the sensing material may be formed by plasma enhanced chemical vapor deposition (PECVD). The term "hydrogenated" in the hydrogenated amorphous silicon means amorphous silicon containing 10-20% of hydrogen ($H_2$). On the other hand, amorphous silicon into which no hydrogen is injected has trap sites that can trap $10^{17}$-$10^8$ electrons (#/cm$^3$). The trap sites hinder the movement or generation of electrons. However, if hydrogen is injected into amorphous silicon, the injected hydrogen is bonded with trap sites inside the amorphous silicon, whereby the number of trap sites can be reduced up to $10^{15}$ (#/cm$^3$). For these reasons, the hydrogenated amorphous silicon is used as the sensing material.

Furthermore, the hydrogenated amorphous silicon used as the sensing material has a band gap in the range of 1.5 eV to 2.1 eV. The band gap means minimum energy necessary to change a material from an electrically neutral state to a state in which excess electrons or holes exist. That is, this means that the hydrogenated amorphous silicon needs external energy of 1.5-2.1 eV in order to excite electrons from a ground state to an excited state. Heat, electricity, or light can be used as the external energy. Optical energy is used in the embodiments of the present invention.

Moreover, if the external energy is applied to the hydrogenated amorphous silicon, electron-hole pair (EHP) is generated within the hydrogenated amorphous silicon. Generally, since the hydrogenated amorphous silicon is n-type semiconductor, it is more efficient to use electron of the EHP.

The hydrogenated amorphous silicon having the above-described physical properties is expressed as variation in the number of electrons generated according to the applied external energy, e.g., the optical energy. For example, when the hydrogenated amorphous silicon is exposed to natural light at noon under fine weather, $10^5$-$10^6$ excited electrons (#/cm$^3$) are generated. Therefore, the hydrogenated amorphous silicon can be used as a high-sensitivity sensing material in an environment where the external energy can be controlled, for example, the quantity of light can be controlled.

As one of methods for measuring a concentration or thickness of a specific material by using the physical properties of the hydrogenated amorphous silicon, the quantity of light is fixed and then a specific material prohibiting the light transmission is placed on the hydrogenated amorphous silicon layer. In this case, the quantity of light transmitted to the hydrogenated amorphous silicon layer is reduced. Hence, the number of the generated electrons, that is, photocurrent, is reduced. At this point, when the concentration or thickness of the specific material hindering the light transmission is changed, the quantity of light transmitted to the hydrogenated amorphous silicon layer is changed, resulting in change of the photocurrent value. By detecting the change of the photocurrent value, the change in the concentration or thickness of the specific material can be measured.

Components of the measured dimensions, for example, the photocurrent, should be understood in order to improve the accuracy of the measured dimensions, that is, the reproduction, when detecting the concentration or thickness of the specific material by measuring the change of the photocurrent value generated according to the quantity of light transmitted to the hydrogenated amorphous silicon layer.

In order to understand the components of the photocurrent generated according to the quantity of light transmitted to the hydrogenated amorphous silicon layer, electrodes are formed on the hydrogenated amorphous silicon layer at a predetermined interval and then a small voltage of 0.5-5 V is applied to the electrodes. If the light transmitted to the hydrogenated amorphous silicon layer is completely blocked in such a state that the voltage is applied, a current flows due to electric charges corresponding to the electrical conductivity of the hydrogenated amorphous silicon layer. This is called a dark conductivity or dark current ($I_d$). A photocurrent component generated in the hydrogenated amorphous silicon layer by the light is not included in the photocurrent. This is set as a default and the hydrogenated amorphous silicon layer is exposed to light by attaching a material hindering the light transmission thereon. In this way, if the hydrogenated amorphous silicon layer changes to a photo conductive state, the light transmission is reduced by an amount of the material absorbed by the hydrogenated amorphous silicon layer, and a photocurrent corresponding to the reduced amount of the light transmission is generated. Since a predetermined voltage is applied to both ends of electrodes, the generated photocurrent flows through one of the electrodes. Since a dark current flows even in the photo conductive state, a total current is equal to a sum of the dark current and the photocurrent. In order to increase the effect of the photocurrent, it is advantageous to lowering the dark current by controlling a voltage. However, it is preferable to make the dark current higher than noise component.

Hereinafter, the preferred embodiments of the present invention will be described with the accompanying drawings.

In the figures, the dimensions of layers and regions are exaggerated for clarity of illustration. It will also be understood that when a layer or film is referred to as being "on" another layer or substrate, it can be directly on the other layer or substrate, or intervening layers may also be present. Like reference numerals refer to like elements throughout the specification.

FIG. 1 illustrates a disease diagnosis principle and a disease diagnosis method in accordance with an embodiment of the present invention.

Referring to FIG. 1(A), a disease diagnosis chip includes a light sensing layer 110, a first probe molecule 150, an electrode 120, a fluid tube 160, and a measuring device 200. The light sensing layer 110 generates a photocurrent according to quantity of light radiated from the outside. The light sensing layer 110 may include hydrogenated amorphous silicon. The first probe molecule 150 is fixed onto the light sensing layer 110. The electrode 120 is connected to the light sensing layer 110 to detect an electric signal corresponding to photoelectric charges of the light sensing layer 110. The fluid tube 160 covers the first probe molecule 150 and guides a sample to the first probe molecule 150. The measuring device 200 is connected to the electrode 120 to measure the photocurrent generated from the light sensing layer 110. The measuring device 200 may include an amperemeter or voltmeter.

Referring to FIG. 1(B), when a solution where the sample containing the target molecule 180 reacts with a second probe molecule 170 to which an enzyme is attached is injected inside the disease diagnosis chip, the solution flows along the fluid tube 160 to a portion where the first probe molecule 150 on the light sensing layer 110 is fixed, forming a complex with the second probe molecule 170 to which the first probe molecule (150)-target molecule (180)-enzyme is attached. The complex forming reaction may be an antigen-antibody reaction.

Referring to a current-time graph, if the disease diagnosis chip is placed in a space where natural light exists in a state that the second probe molecule 170 with the first probe molecule (150)-target molecule (180)-enzyme attached forms a complex, a predetermined photocurrent is generated with time. Instead of the natural light, an indoor fluorescent lamp or light with a specific single wavelength may be used. At this point, a value of $I_p/I_d$ may be changed according to the intensity of light radiated onto the disease diagnosis chip. $I_p$ represents a magnitude of a photocurrent generated when the light exists, and $I_d$ represents a magnitude of a photocurrent generated in a dark state.

Referring to FIG. 1(C), if a chromogenic reagent, e.g., a precipitate inducing reagent, which can generate a precipitate by reacting with the enzyme fixed to the second probe molecule 170 of the complex, flows along the fluid tube 160, a precipitate layer 190 is formed on the light sensing layer 110 to which the first probe molecule 150 is fixed.

For example, if HPR is used as the enzyme attached to the second probe molecule 170, the precipitate layer can be formed using a mixed solution of 4-CN(4-chloronaphtol)+ $H_2O_2$ as the chromogenic reagent. AT this point, it takes about 1-5 minutes to form the precipitate layer.

Referring to a current-time graph, the precipitate layer 190 is formed on the light sensing layer 110, and light radiated onto the light sensing layer 110 is partially blocked. Thus, a photocurrent is reduced compared with the photocurrent generated in the case of FIG. 1(B). Since a thickness of the precipitate layer 190 is proportional to the amount of the target molecule 180, the quantity of light blocked by the precipitate layer 190 is inversely proportional to the amount of the target molecule 180. Consequently, the magnitude of the generated photocurrent is inversely proportional to the amount of the target molecule 180, that is, the concentration of the target molecule 180. Using the above-described correlation, the concentration of the target molecule 180 can be easily measured by comparing the photocurrent value obtained after the measurement of the sample with a target molecule concentration-photocurrent standard curve previously measured.

Figure 2:
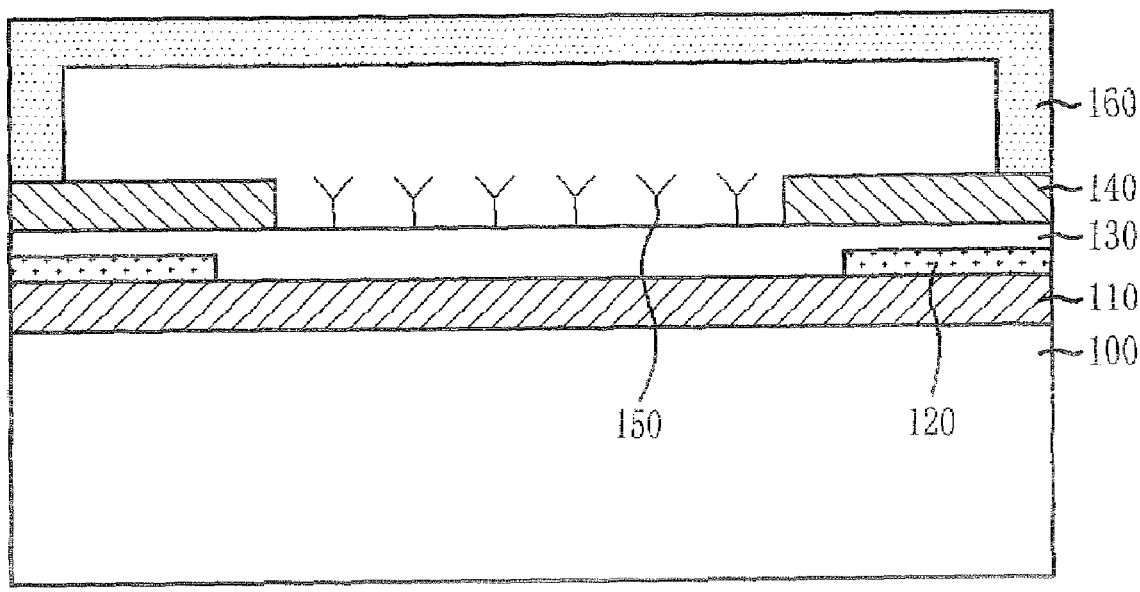
FIG. 2 is a cross-sectional view of a disease diagnosis chip using the disease diagnosis principle in accordance with the embodiment of the present invention.

FIG. 2 is a cross-sectional view of the disease diagnosis chip using the disease diagnosis principle in accordance with the embodiment of the present invention.

Referring to FIG. 2, the disease diagnosis chip includes the light sensing layer 110, the first probe molecule 150 fixed on the light sensing layer 110, and the electrode 120 connected to the light sensing layer 110 to detect the electric signal corresponding to the photoelectric charges of the light sensing layer 110. The light sensing layer 110 may be formed of hydrogenated amorphous silicon.

The disease diagnosis chip may further include a light transmitting layer 130 covering the light sensing layer 110 and the electrode 120. The light transmitting layer 130 may be formed of a transparent insulating material that can insulate the electrode 120 and transmit light to the light sensing layer 110. Examples of the transparent insulating layer include silicon oxide ($SiO_2$).

The first probe molecule 150 may be formed of a material selected from the group consisting of antigen, antibody, DNA, RNA, lectin, protein, peptides, and saccharide. The first probe molecule 150 may be fixed to the light sensing layer 110 or the light transmitting layer 130.

In addition, the disease diagnosis chip may further include a light blocking layer 140 in a region other the region where the first probe molecule 150 on the light sensing layer 110 is fixed. The light blocking layer 140 prevents the photocurrent from being generated in the region other than the light sensing layer 110 region for substantially detecting the target molecule and measuring the concentration of the target molecule, thereby improving the reproduction of the disease diagnosis chip.

The disease diagnosis chip may further include the fluid tube 160 covering the region where the first probe molecule 150 is formed, and guiding the introduced sample to the region where the first probe molecule 150 is fixed. The fluid tube 160 effectively controls the delivery, stop and junction of the sample so that the target molecule such as protein inside the disease diagnosis chip can be delivered just like a lamina flow. The smooth delivery of the target molecule can improve the reproduction of the disease diagnosis chip.

The fluid tube 160 may be formed of a light transmitting material selected from the group consisting of polycarbonate (PC), polymethyl methacrylate (PMMA), polydimethylsiloxane (PDMS), and cyclic olefin copolymer (COC)

By using hydrogenated amorphous silicon as the sensing material of the light sensing layer, the sensing sensitivity of the disease diagnosis chip can be improved.

Furthermore, the formation of the fluid tube can improve the reproduction of the disease diagnosis chip. The reproduction of the disease diagnosis chip can be further improved by forming the light blocking layer in the region other than the region where the reaction occurs actually.

FIGS. 3A to 3D are cross-sectional views illustrating a method for manufacturing a disease diagnosis chip in accordance with an embodiment of the present invention.

Figure 3A:
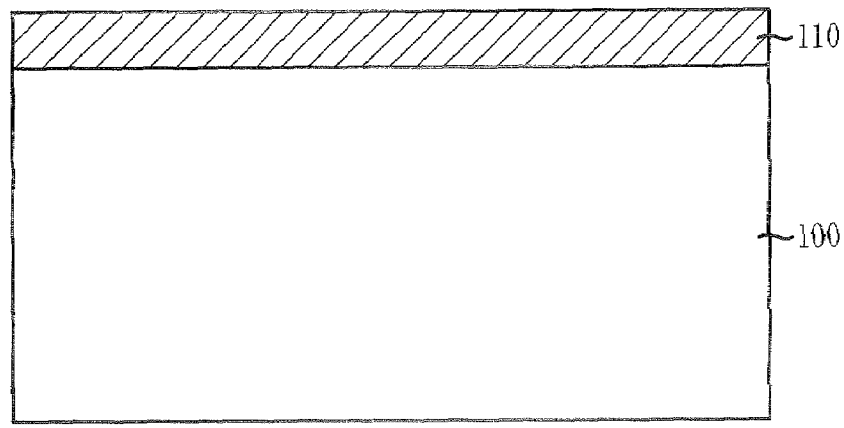
FIGS. 3A to 3D are cross-sectional views illustrating a method for manufacturing a disease diagnosis chip in accordance with an embodiment of the present invention.

Referring to FIG. 3A, a light sensing layer 110 is formed on a substrate 100. The light sensing layer 110 may be formed of hydrogenated amorphous silicon by plasma enhanced chemical vapor deposition (PECVD). The term "hydrogenated" in the hydrogenated amorphous silicon means amorphous silicon containing 10-20% of hydrogen. The injection of hydrogen into amorphous silicon reduces trap site that hinders the movement and generation of electrons of the amorphous silicon layer, thereby improving the sensing sensitivity of the disease diagnosis chip.

Figure 3B:
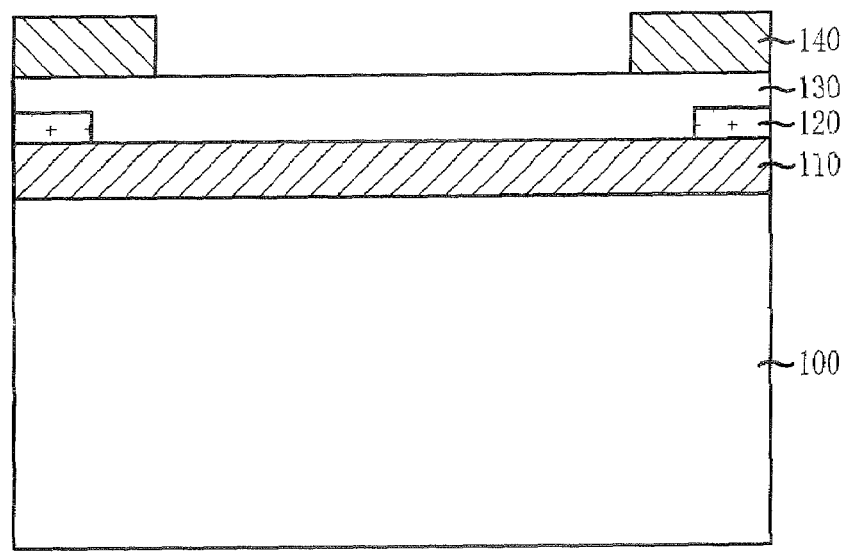

Referring to FIG. 3B, electrodes 120 are formed on the light sensing layer 110. The electrodes 120 may be separated in the range of 0.1-1.0 mm at both ends of the light sensing layer 110. The electrodes 120 may be formed of doped polysilicon, conductive metal nitride, metal, or metal silicide.

A light transmitting layer 130 is formed to cover the electrodes 120 and the light sensing layer 110. The light transmitting layer 130 insulates the electrodes 120 from each other and may be formed of silicon oxide. The light transmitting layer 130 should be formed of a material that can transmit light up to the light sensing layer 110. Therefore, the light transmitting layer 130 is preferably formed of an insulating material that can transmit light.

Through a subsequent process, a light blocking layer 140 is formed on the light transmitting layer 130 in a region other than a region where a probe molecule is to be fixed. The light blocking layer 140 prevents the transmission of light in the region other than the region that is sensed by the actual reaction. Thus, in detecting the target molecule and measuring the concentration of the target molecule, the accuracy of the measured dimensions can be improved. To effectively block the light, the light blocking layer 140 can be formed of any material only if the material can completely absorb or reflect the radiated light.

Figure 3C:
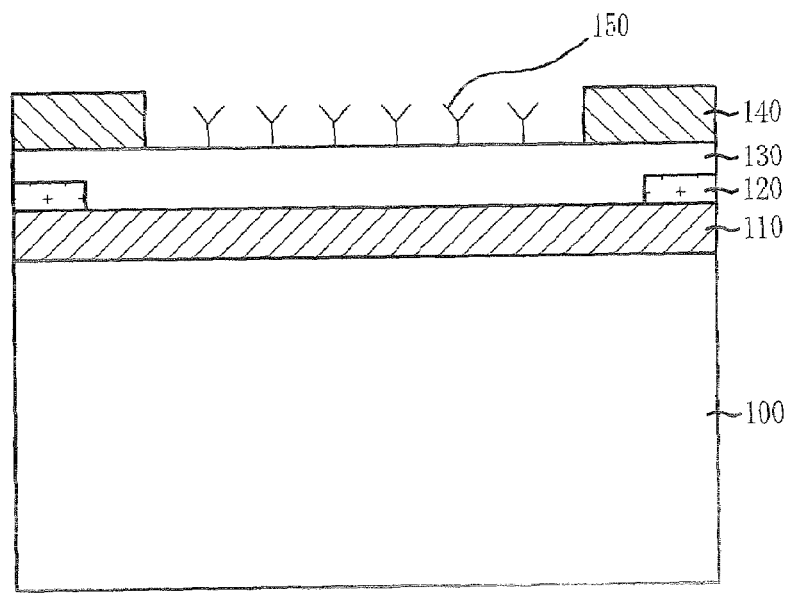

Referring to FIG. 3C, a first probe molecule 150 is fixed on the light transmitting layer 130 between the electrodes 120. The first probe molecule 150 may be formed of a material selected from the group consisting of antigen, antibody, DNA, RNA, lectin, protein, peptides, and saccharide. As one of methods for fixing the first probe molecule 150 on the light transmitting layer 110, a linker molecule suitable for the first probe molecule 150 is selected and fixed to the light transmitting layer 130, and the first probe molecule 150 is then fixed to the light transmitting layer 130.

Figure 3D:
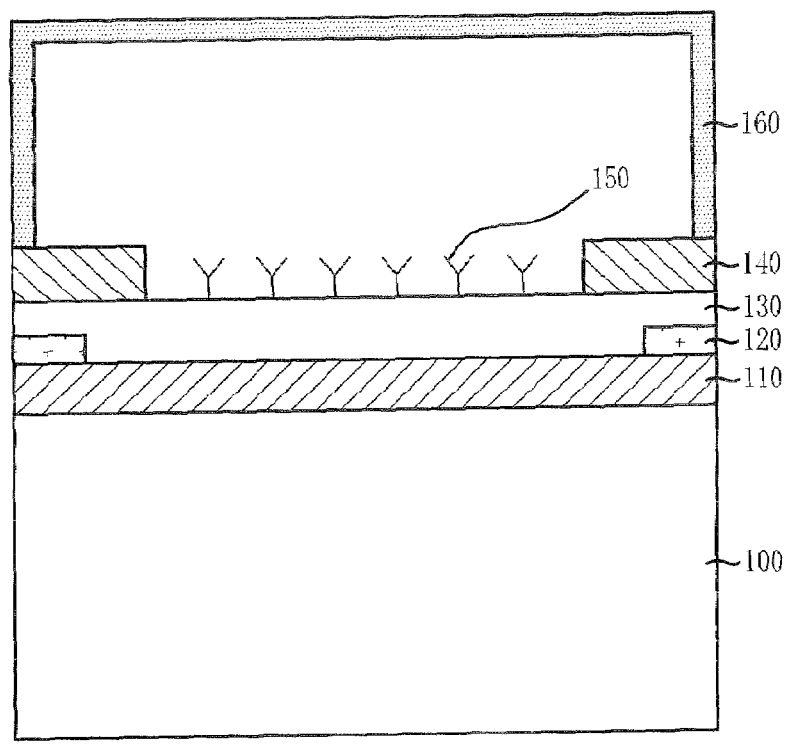

Referring to FIG. 3D, a fluid tube 160 is formed on the light sensing layer 110 to cover the first probe molecule 150 and guide a sample to the first probe molecule 150. The fluid tube 160 may be formed of a light transmitting material selected from the group consisting of polycarbonate (PC), polymethyl methacrylate (PMMA), polydimethylsiloxane (PDMS), and cyclic olefin copolymer (COC).

Figure 4:
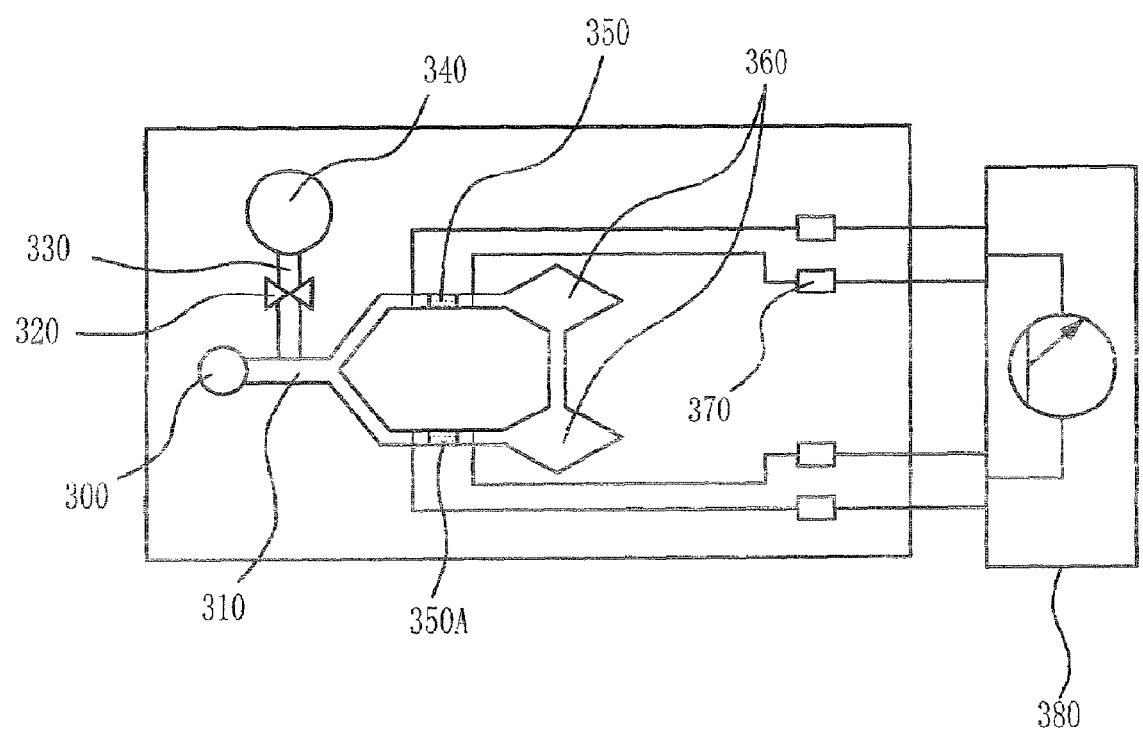
FIG. 4 is a cross-sectional view of a disease diagnosis apparatus using the disease diagnosis principle in accordance with the embodiment of the present invention.

FIG. 4 is a cross-sectional view of a disease diagnosis apparatus using the disease diagnosis principle in accordance with the embodiment of the present invention.

Referring to FIG. 4, disease diagnosis chips 350 and 350A are fixed inside a body. The body includes a sample inlet 300, a channel guiding the sample to the disease diagnosis chips 350 and 350A, and a photocurrent measuring device 380 measuring a photocurrent generated from the disease diagnosis chips 350 and 350A. Although not shown, each of the disease diagnosis chips 350 and 350A may include a light sensing layer, a probe molecule fixed on the light sensing layer, and an electrode connected to the light sensing layer to detect an electric signal corresponding to photoelectric charges of the light sensing layer (see FIG. 2).

In addition, the disease diagnosis apparatus may further include a first storage 340 storing a chromogenic reagent for inducing the generation of precipitate, a valve 320 controlling the introduction of the chromogenic reagent, a first channel 330 through which the chromogenic reagent passes, a second storage 360 storing solutions passing through the disease diagnosis chips 350 and 350A, and electrodes 370 through which the electric signals of the disease diagnosis chips pass to the photocurrent measuring device.

Additionally, the disease diagnosis apparatus may further include a plurality of disease diagnosis chips 350 and 350A for determining if a plurality of diseases exist. At least one of the disease diagnosis chips 350 and 350A can be used as a test chip for testing if an error exists in the antigen-antibody reaction.

Moreover, the photocurrent measuring device 380 may further have a function of converting the photocurrent value into a quantitative digital value.

The disease diagnosis apparatus 380 with a plurality of disease diagnosis chips can perform a multiplexing detection that simultaneously diagnoses a plurality of diseases.

Since the disease diagnosis apparatus outputs the test results expressed as the quantitative digital value, an error can be reduced when the users determine the test results.

In accordance with the present invention, the target molecule can be detected and the concentration of the target molecule can be measured. In particular, the concentration of the target molecule used as an important factor in disease diagnosis is expressed as the quantitative value. Thus, an error is reduced when the users determine the test results.

Moreover, since the sample moves through the fluid tube, the target molecule smoothly moves, thereby improving the reproduction.

While the present invention has been described with respect to the specific embodiments, it will be apparent to those skilled in the art that various changes and modifications may be made without departing from the spirit and scope of the invention as defined in the following claims.

What is claimed is:

1. A disease diagnosis chip, comprising:
   a light sensing layer formed of hydrogenated amorphous silicon;
   a probe molecule fixed on the light sensing layer; and
   an electrode formed on a top surface of the light sensing layer for detecting an electric signal corresponding to photoelectric charges of the light sensing layer, the top surface facing the probe molecule.

2. The disease diagnosis chip of claim 1, further comprising:
   a light transmitting layer disposed on the light sensing layer to cover the electrode and the light sensing layer.

3. The disease diagnosis chip of claim 2, wherein the light transmitting layer is formed of silicon dioxide ($SiO_2$).

4. The disease diagnosis chip of claim 1, further comprising:
   a light blocking layer disposed on the light sensing layer in a region other than a region where the probe molecule is fixed.

5. The disease diagnosis chip of claim 1, further comprising:
   a fluid tube covering the probe molecule and guiding an introduced sample to the probe molecule.

6. The disease diagnosis chip of claim 5, wherein the fluid tube is formed of a light transmitting material.

7. The disease diagnosis chip of claim 5, wherein the fluid tube is formed of a material selected from the group consisting of polycarbonate (PC), polymethyl methacrylate (PMMA), polydimethylsiloxane (PDMS), and cyclic olefin copolymer (COC).

8. The disease diagnosis chip of claim 1, wherein the probe molecule is formed of a material selected from the group consisting of antigen, antibody, DNA, RNA, lectin, protein, peptides, and saccharide.

9. The disease diagnosis chip of claim 1, further comprising:
an amperemeter or voltmeter measuring the electric signal corresponding to an electric signal corresponding to the photoelectric charges generated from the light sensing layer.

10. A disease diagnosis apparatus, comprising:
a disease diagnosis chip including:
a light sensing layer formed of hydrogenated amorphous silicon;
a probe molecule directly fixed on the light sensing layer; and
an electrode formed on a top surface of the light sensing layer for detecting an electric signal corresponding to photoelectric charges of the light sensing layer, the top surface facing the probe molecule; and
a body in which the disease diagnosis chip is fixed, the body including:
a sample inlet where a sample is introduced;
a channel for guiding the introduced sample to the disease diagnosis chip; and
a measuring device for measuring a photocurrent generated from the disease diagnosis chip.

11. The disease diagnosis apparatus of claim 10, wherein two or more disease diagnosis chips are provided for determining if a plurality of diseases exist and measuring the target molecule.

12. The disease diagnosis apparatus of claim 11, wherein at least one of the two or more disease diagnosis chips is a test chip for testing if an error occurs in an antigen-antibody reaction.

13. The disease diagnosis apparatus of claim 10, wherein the measuring device has a function of converting the measured photocurrent value into a quantitative digital value.

* * * * *